United States Patent
Weng et al.

(10) Patent No.: US 9,706,098 B2
(45) Date of Patent: Jul. 11, 2017

(54) INSPECTION SYSTEM AND METHOD FOR OBTAINING AN ADJUSTED LIGHT INTENSITY IMAGE

(71) Applicant: CHROMA ATE INC., Tao-Yuan (TW)

(72) Inventors: Yi-Lung Weng, Tao-Yuan (TW); Chien-Hsun Chu, Tao-Yuan (TW)

(73) Assignee: CHROMA ATE INC., Tao-Yuan (TW)

( * ) Notice: Subject to any disclaimer, the term of this patent is extended or adjusted under 35 U.S.C. 154(b) by 0 days.

(21) Appl. No.: 14/958,904

(22) Filed: Dec. 3, 2015

(65) Prior Publication Data

US 2016/0165110 A1    Jun. 9, 2016

(30) Foreign Application Priority Data

Dec. 4, 2014    (TW) .............................. 103142200 A

(51) Int. Cl.
*H04N 5/225*    (2006.01)
*H04N 5/235*    (2006.01)
*H04N 17/00*    (2006.01)

(52) U.S. Cl.
CPC ......... *H04N 5/2256* (2013.01); *H04N 5/2354* (2013.01); *H04N 17/002* (2013.01)

(58) Field of Classification Search
CPC .. H04N 5/2256; H04N 5/2354; H04N 17/002; G06K 9/4661; G06K 9/4604
USPC .................................................. 348/370, 371
See application file for complete search history.

(56) References Cited

U.S. PATENT DOCUMENTS

| 6,450,664 B1 | 9/2002 | Kelly | |
| 2005/0265014 A1* | 12/2005 | Matsui | G03B 15/05 362/5 |
| 2006/0193622 A1* | 8/2006 | Endo | G03B 7/16 396/157 |
| 2013/0120636 A1* | 5/2013 | Baer | G03B 15/05 348/335 |

FOREIGN PATENT DOCUMENTS

| TW | I342510 B | 5/2011 |
| TW | M417626 U | 12/2011 |
| TW | 201317549 A | 5/2013 |

* cited by examiner

*Primary Examiner* — Albert Cutler
(74) *Attorney, Agent, or Firm* — CKC & Partners Co., Ltd.

(57) ABSTRACT

An inspection system for obtaining an adjusted light intensity image includes a light source, an image capturing device and a controller. A field of view of the image capturing device is adjusted within an illumination area of the light source. A plurality of light emitting units of the light source are turned on in sequence. The image capturing device captures a calibration image when each of the light emitting units is turned on to obtain a plurality of the calibration images. The controller adjusts the light emitting intensities of the light emitting units respectively according to the light intensity distributions of the calibration images to obtain a specific intensity distribution of an inspection image in the field of view and compensate a vignette effect of the image capturing device.

9 Claims, 5 Drawing Sheets

INSPECTION SYSTEM AND METHOD FOR OBTAINING AN ADJUSTED LIGHT INTENSITY IMAGE

RELATED APPLICATIONS

This application claims priority to Taiwan Application Serial Number 103142200, filed Dec. 4, 2014, which is herein incorporated by reference.

BACKGROUND

Field of Disclosure

The present disclosure relates to an image inspection system, and particularly, to an inspection system for obtaining an adjusted light intensity image.

Description of Related Art

An inspection system uses a light source to illuminate a sample under test and capture an image thereof, so as to inspect the quality of the sample. Nowadays, a lens is mostly used to capture the image of the sample under test. However, the intensity of light decreases as being closer to an edge of the field of view of the lens after the light passes through the lens, and thus details of the image at the edge of the field of view s hard to be analyzed. Although the light intensity of the image can be compensated by a function of vignetting calibration of a software, the noise of the image at the edge is simultaneously increased, and thus a S/N ratio can not substantially be improved. With a development of technology and products changed overtime, demands on an illuminance and a stability of the inspection system are increasing. Therefore, how to design the inspection system to improve the aforementioned drawbacks is an urgent problem to be solved in industry.

SUMMARY

One aspect of the present disclosure is to provide a method for an inspection system obtaining an adjusted light intensity image. The inspection system includes a light source, an image capturing device, and a controller. The method includes adjusting a field of view of the image capturing device to be within an illumination area of the light source. A plurality of light emitting units of the light source are turned on in sequence. A calibration image is captured by the image capturing device when each of the light emitting units is turned on so as to obtain a plurality of calibration images. Light emitting intensities of the light emitting units are adjusting respectively by the controller according to light intensity distributions of the calibration images, so as to obtain an inspection image in the field of view having a specific light intensity distribution.

Another aspect of the present disclosure is to provide an inspection system for obtaining an adjusted light intensity image. The inspection system includes a light source, an image capturing device, and a controller. The light source includes a plurality of light emitting units. The light source has an illumination area. The image capturing device has a field of view smaller than the illumination area. The controller is electrically connected to the image capturing device and the light source. The image capturing device is controlled to capture a calibration image when each of the light emitting units is turned on, so as to obtain a plurality of calibration images. Light emitting intensities of the light emitting units are adjusted respectively according to light intensity distributions of the calibration images, so as to obtain an inspection image in the field of view having a specific light distribution.

DETAILED DESCRIPTION

Figure 1:
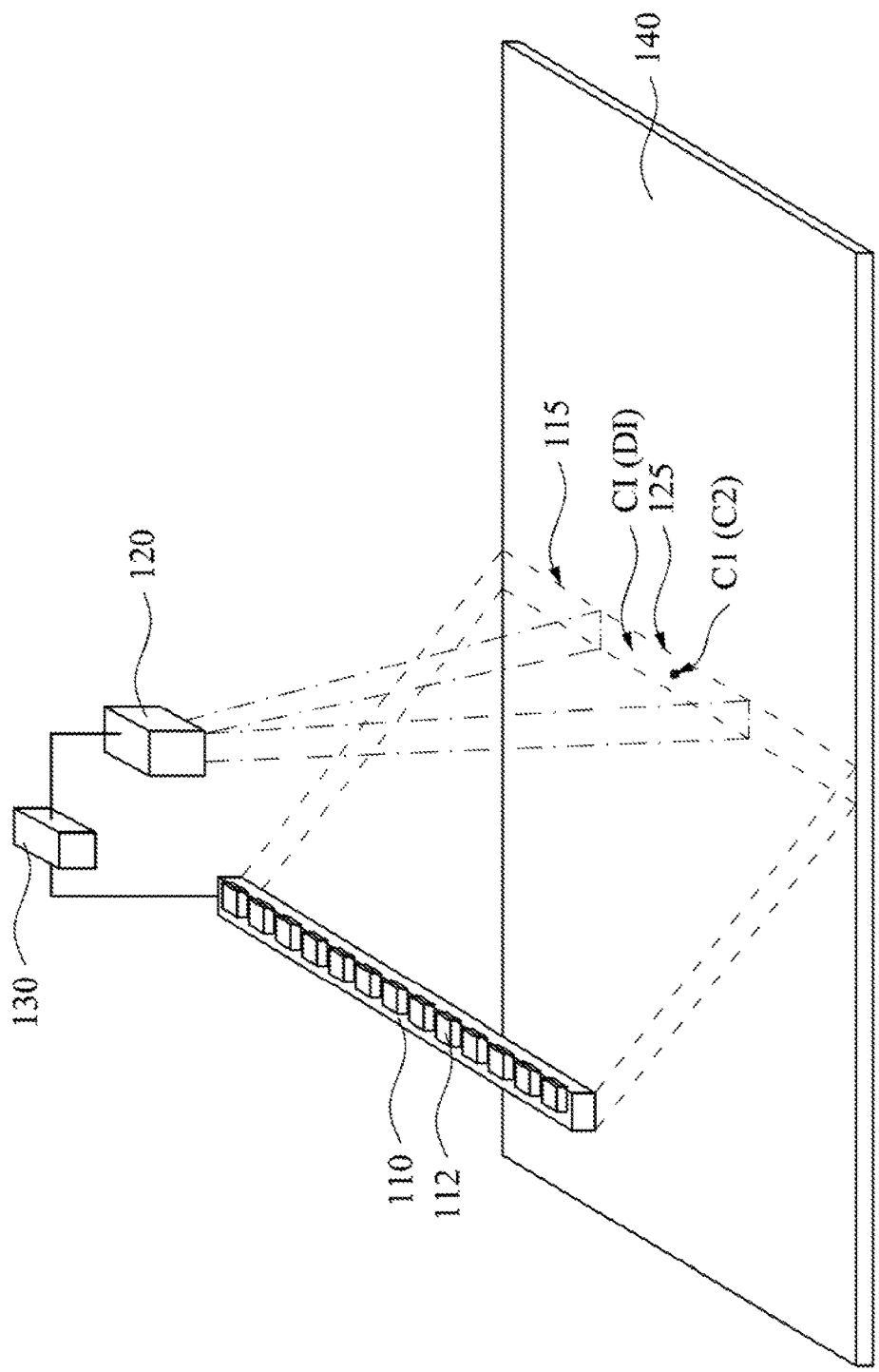
FIG. 1 is a schematic diagram of an inspection system with an adjusted light source according to an embodiment of the present disclosure.

Reference will now be made in detail to the present embodiments of the disclosure, examples of which are illustrated in the accompanying, drawings. Wherever possible, the same reference numbers are used in the drawings and the description to refer to the same or like parts.

FIG. 1 is a schematic diagram of an inspection system with an adjusted light source according to an embodiment of the present disclosure. As shown in FIG. 1, the inspection system includes a light source 110, an image capturing device 120, and a controller 130. The light source 110 includes a plurality of light emitting units 112. The light source 110 has an illumination area 115, in which a centroid of the illumination area 115 is defined as a center C1 of the illumination area 115. The image capturing device 120 has a field of view 125, in which a centroid of the field of view 125 is defined as a center C2 of the field of view 125. The field of view 125 is smaller than the illumination area 115. The controller 130 is electrically connected to the image capturing device 120 and the light source 110. The image capturing device 120 is controlled to capture a calibration image CI when each of the light emitting units is turned on, so as to obtain a plurality of the calibration images CI. Light emitting intensities of the light emitting units 112 are adjusted respectively according to light intensity distributions of the calibration images CI, so as to obtain an inspection image DI in the field of view 125 having a specific light intensity distribution (e.g. a uniform light intensity distribution). Moreover, the light emitting units 112 are illustrated as a solid line in FIG. 1 for the sake of clarity. The inspection image DI is an image captured by the image capturing device 120 when the inspection system inspects samples.

Briefly speaking, the inspection system in this embodiment of the present disclosure can respectively controls the light emitting intensities of the light emitting units 112 in accordance with the field of view 125 of the image capturing device 120, such that the inspection image DI in the field of view 125 has the specific light intensity distribution. For example, the uniform light intensity distribution is formed. Due to a vignetting effect of the image capturing device 120, the light intensity at an edge of the field of view 125 is lower than the light intensity at a center C2 of the field of view 125. The controller 130 can respectively adjust the light emitting intensities of the light emitting units 112, for example, the light emitting units 112 that illuminates the edge of the field of view 125 has higher light emitting intensities than the light emitting units 112 that illuminates the center C2 of the field of view 125 do, such that the darkened inspection image DI resulted from the vignetting of the image capturing device 120 is compensated, and the inspection image DI in the field of view 125 has the uniform light intensity distribution. As a result, a S/N ratio at the edge of the inspection image DI can be improved. In addition, the controller 130 can respectively control each of the light emitting units 112, and thus even a location or a size of the field of view 125 of the image capturing device 120 is changed, the controller 130 can still adjust the light emitting intensities of the light emitting units 112 respectively according to the location or the size of the field of view 125, such that the inspection image DI in the field of view 125 has the specific (e.g. uniform) light intensity distribution. That is, the inspection system in the embodiment can be applied to image capturing devices 120 with different vignetting effects without changing the light source 110.

In this embodiment, the light source 110 may be a linear light source, that is, the light emitting units 112 are arranged in a straight line, and the inspection system may be a linear scanning system, for example. In other words, a sample under test (not shown) can be disposed on a measuring stage 140, and the light source 110 can obliquely illuminate the sample under test. After a calibration of the light source 110 is finished, portions of the inspection image DI of the sample under test can be sequentially captured in the field of view 125 by moving the sample. If the sample under test needs to be illuminated by light with the specific light intensity distribution, the light source 110 can respectively control each of the light emitting units 112 according to a desired light intensity distribution, such that the inspection image DI in the field of view 125 has the specific light intensity distribution. Therefore, the inspection system of this embodiment also can flexibly control the light intensity distribution of the inspection image DI. In addition, each of the light emitting units 112 can be a single light-emitting diode (LED) or a plurality of LEDs. The image capturing device 120 can include a lens, and the reduced light intensity of the image due to the vignetting can be compensated by the controller 130 which controls the light emitting intensities of the light emitting units 112. Then, the inspection system can inspect the sample under test. More specifically, when the inspection system inspects the sample under test, the controller 130 turns on all of the light emitting units 112 and controls the image capturing system 120 to capture the inspection image DI.

Figure 2:
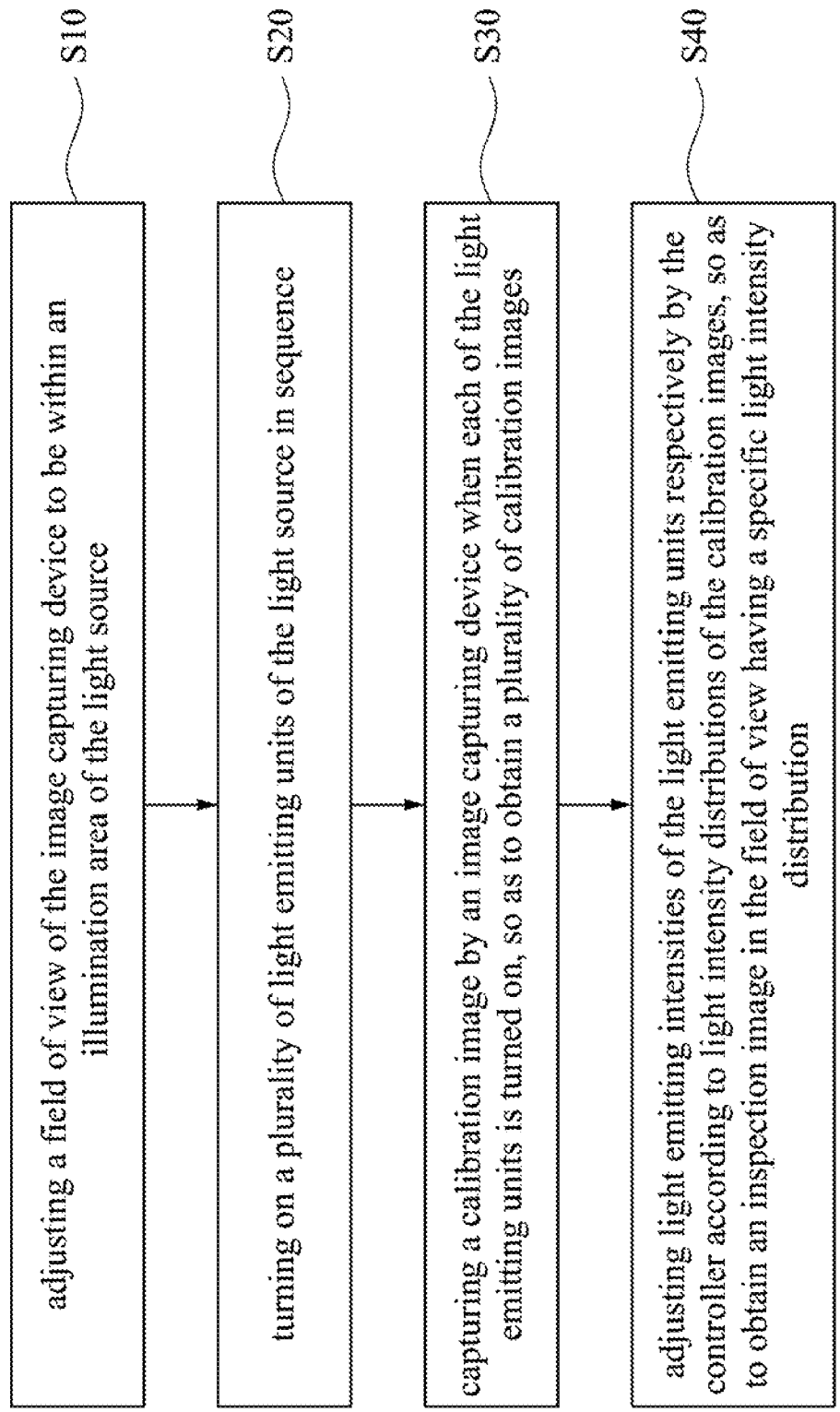
FIG. 2 is a flow chart of a method for calibrating a light source of the inspection system of FIG. 1 according to one embodiment of the present disclosure.

Reference is made to FIGS. 1 and 2. FIG. 2 is a flow chart of a method for calibrating a light source of the inspection system of FIG. 1 according to one embodiment of the present disclosure. First, as shown in step S10, the field of view 125 of the image capturing device 120 is adjusted to be within the illumination area 115 of the light source 110. Next, as shown in step S20, a plurality of the light emitting units 112 of the light source 110 are turned on in sequence. Then, as shown in step S30, the image capturing device 120 captures the calibration images CI when each of the light emitting units 112 is turned on, so as to obtain a plurality of the calibration images CI. Thereafter, as shown in step S40, the controller 130 adjusts the light emitting intensities of the light emitting units 112 respectively according to the light intensity distributions of the calibration images CI so as to obtain the inspection image DI in the field of view 125 having the specific (e.g. uniform) light intensity distribution.

In this embodiment, the illumination area 115 represents an area on the measuring stage 140 in which the area is illuminated by all of the turned-on light emitting units 112 of the light source 110. It is necessary to adjust the field of view 125 to be within, the illumination area 115 first, as shown in step S10. Then, the fight intensity of the image captured in the field of view 125 by the image capturing device 120 can be adjusted by changing the light emitting intensities of each of the light emitting units 112.

Next, as shown in step S20, a plurality of the light emitting units 112 are turned on in sequence. And as shown in step S30, the image capturing device 120 captures the calibration images CI when each of the light emitting units 112 is turned on, so as to obtain a plurality of the calibration images CI. More specifically, when one of the light emitting units 112 is turned on, the image capturing device 120 captures the calibration image CI, and the calibration image CI represents the light intensity distribution in the field of view 125, in which the light intensity distribution is contributed from the light emitting unit 112. Different calibration images CI (corresponding to different light emitting units) have different light intensity distributions in the field of view 125. Moreover, as for the same light emitting intensities of the light emitting units 112, when the light emitting unit 112 illuminates the center C2 of the field of view 125 is turned on, the captured image I has a higher light intensity; and when the light emitting unit 112 illuminates the edge of the field of view 125, the captured image I has a lower light intensity due to the vignetting effect of the image capturing device 120.

Thereafter, as shown in step S40, the controller 130 respectively adjusts the light emitting intensities of the light emitting units 112 according to the light intensity distributions of the calibration images CI such that the inspection image DI in the field of view 125 has the specific light intensity distribution. For example, the uniform light intensity distribution is formed (i.e. the vignetting effect is improved), the light emitting intensity of the light emitting unit 112 corresponding to the edge of the field of view 125 can be higher than the light emitting intensity of the light emitting unit 112 corresponding to the center C2 of the field of view 125, such that the vignetting effect of the image capturing device 120 is compensated, and the inspection image DI in the field of view has the uniform light intensity distribution.

The above contexts give examples aim at improving the vignetting effect, however, in some other embodiments, the method for calibrating the light source can be applied to form specific light intensity distributions of inspection images DI depending on different samples under test.

The following examples describe an effect of the aforementioned method for calibrating the light source. FIG. 3A is a light intensity distribution of the illumination area 115 before and after the light source is calibrated according to one example. In this example, a length of the illumination area 115 was about 200 mm, in which an origin of an x-coordinate of FIG. 3A represented the center C1 of the illumination area 115, and the center C1 was defined as the centroid of the illumination area 115. Reference is made to FIGS. 1 and 3A, curve 910 represented a light intensity distribution of the illumination area 115 when all of the light emitting units 112 were turned on and before the light source 110 is calibrated. The light intensity distribution had a maximum in the center C1 of the illumination area 115, and the light intensity decreased as a distance from the center C1 increased due to a limited working distance of the light source 110.

Next, the controller 130 respectively adjusted the light emitting intensities of the light emitting units 112, such that the illumination area 115 of the light source 110 had a light intensity distribution shown as curve 920 or curve 930. That is, the light emitting unit 112 corresponding to the center C1 of the illumination area 115 had a lower light emitting intensity, while the light emitting units 112 corresponding to the edge of the illumination area 115 had higher light emitting intensities. The curve 920 and the curve 930 respectively represented light intensity distributions obtained by the calibrated light source 110 in different situations. For example, the curve 930 represented a maximum compensation value of the corrected vignetting under a maximum illuminance of the center C1 of the illumination area 115. Moreover, difference between the maximum point of the curve 920 (930) and the minimum point at the center C1 of the curve 920 (930) represented a compensation ability of the light intensity of the light source 110.

Figure 3B:
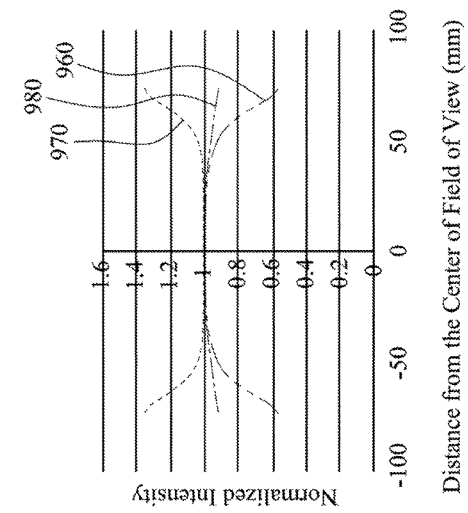
FIG. 3B is a light intensity distribution of the field of view before and after the light source was calibrated according to one example.
Figure 3A:
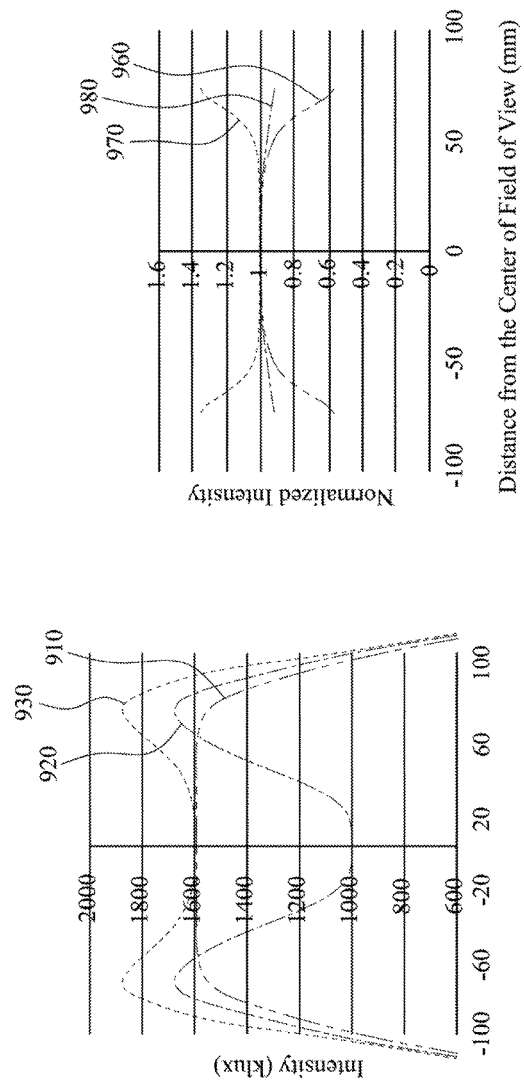
FIG. 3A is a light intensity distribution of an illumination area before and after the light source was calibrated according to one example.

Next, FIG. 3B is normalized light intensity distributions of the field of view 125 before and after the light source 110 was calibrated according to one example. In this example, a length of the field of view 125 was about 150 mm, in which an origin of an x-coordinate of FIG. 3B represented the center C2 of the field of view 125. Reference is made to FIGS. 1 and 3B, in this example, before the light source 110 was calibrated, the normalized light intensity distribution of an image captured by the image capturing device 120 was shown as curve 960. More specifically, the light intensity at the edge of the field of view 125 as decreased due to the working distance of the light source 110 and the vignetting effect of the lens, and such light intensity distribution resulted in the S/N ratio of the image at the edge of the field of view being too small.

The normalized light intensity distribution of the light source 125 was shown as curve 970 in FIG. 3B, in which the controller 130 respectively adjusted the light emitting intensities of the light emitting units 112 to compensate for the light intensity that was too low at the edge of the field of view 125. Curve 980 represented a normalized light intensity distribution (i.e. a cross product of the curve 960 and the curve 970) captured by the image capturing device 120 after the light source 110 was calibrated. The normalized light intensity distribution had a uniform light intensity distribution, and thus the S/N ratio of the image at the edge of the field of view 125 could be effectively improved.

Figure 4:
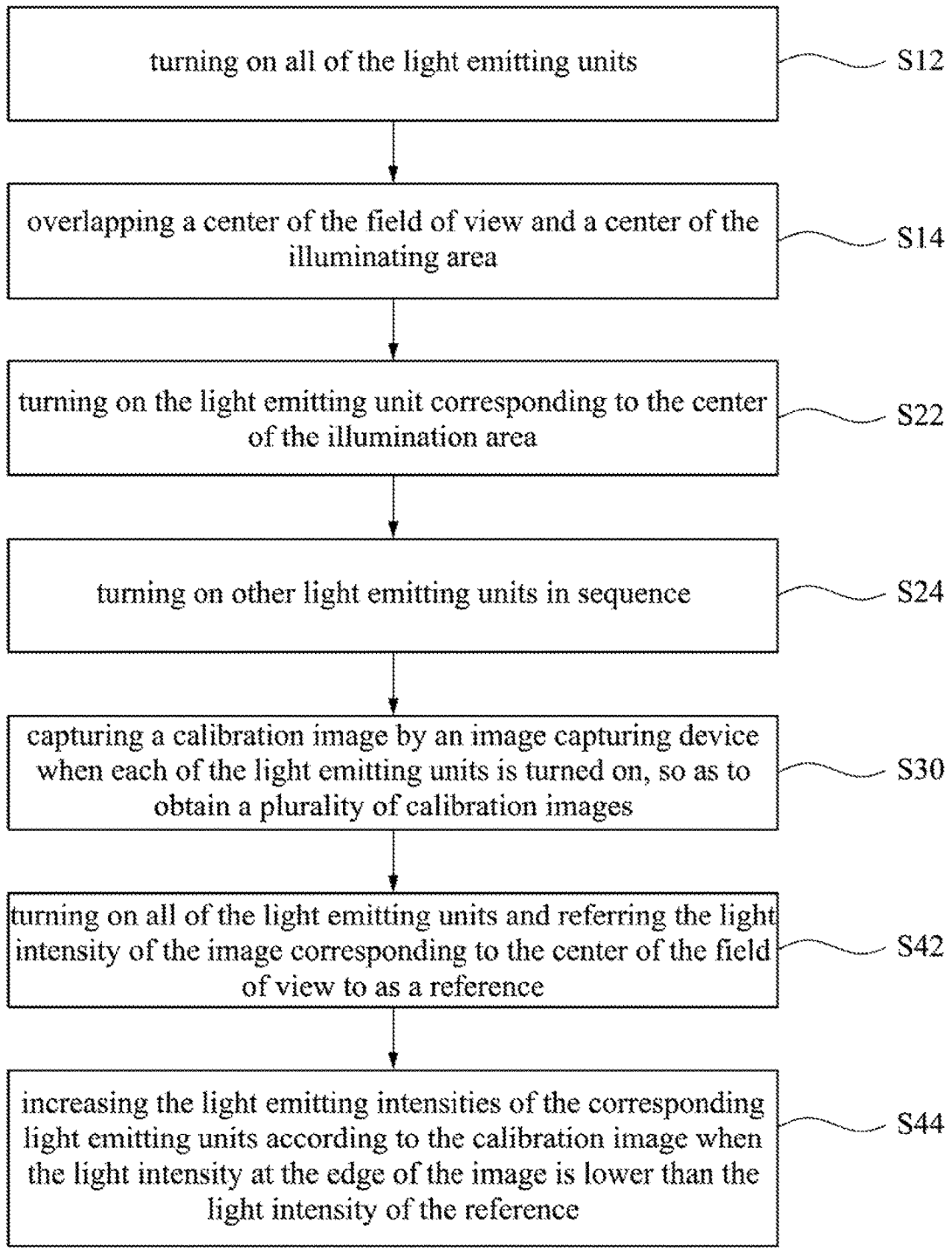
FIG. 4 is a flowchart of a method for calibrating the light source of the inspection system of FIG. 1 according to another embodiment of the present disclosure.

FIG. 4 is a flowchart of a method for calibrating the light source 110 of the inspection system of FIG. 1 according to another embodiment of the present disclosure. Reference is made to FIGS. 1 and 4. In this embodiment, details of step S10 in FIG. 2 are described from step S12. All of the light emitting units 112 are turned on, and thus a location of the illumination area 115 is defined on the measuring stage 140. Then, as shown in step S14, the center C2 of the field of view 125 and the center C1 of the illumination area 115 are overlapped, so as to determine a location of the field of view 125. The step S14 can be achieved by changing a relative position between the light source 110 and the image capturing device 120, changing an illumination method of the light source 110, or changing a location of the field of view 125 of the image capturing device 120.

Thereafter, details of the step S20 in the FIG. 2 are described from step S22. The light emitting unit 112 corresponding to the center C1 of the illumination area 115 is turned on, in which the light emitting unit 112 corresponding to the center C1 affects the light intensity distribution of the illumination area 115 most. Furthermore, since the center C1 and the center C2 are overlapped, the light emitting unit 112 corresponding to center C1 also affects the field of view 125 most. Then, as shown in step S24, the other light emitting units 112 are turned on in sequence. For example, in this embodiment, the light emitting units 112 closer to the center C1 affects the field of view 125 more, and thus the light emitting units 112 can be turned on in sequence from the center C1 to the two opposite sides, so as to respectively obtain the light intensity of the field of view 125, in which the light intensity is affected by each of the light emitting units 112, as shown in step S30. However, the aforementioned steps are only examples, in other embodiments, it is not necessary to turn on the light emitting unit 112 corresponding to the center C1 before turning on the other light emitting units 112. Basically, an embodiment falls within the claimed scope as long as the calibration images C1 of the light emitting units 112 can be obtained.

Next, details of the step S40 in FIG. 2 are described from step S42. All of the light emitting units 112 are turned on, and the light intensity of the image corresponding to the center C2 of the field of view 125 is referred to as a reference. Then, as shown in step S44, when the light intensity at the edge of the image is lower than the light intensity of the reference, the light emitting intensities of the corresponding light emitting units 112 are increased according to the calibration image CI. As mentioned above, the farther away from the center C1, the light intensity of the obtained image becomes lower due to the vignetting effect of the image capturing device 120. Therefore, according to the light intensity distributions of the calibration images CI and the reference, the light emitting intensities of the corresponding light emitting units 112 can be increased.

Figure 5:
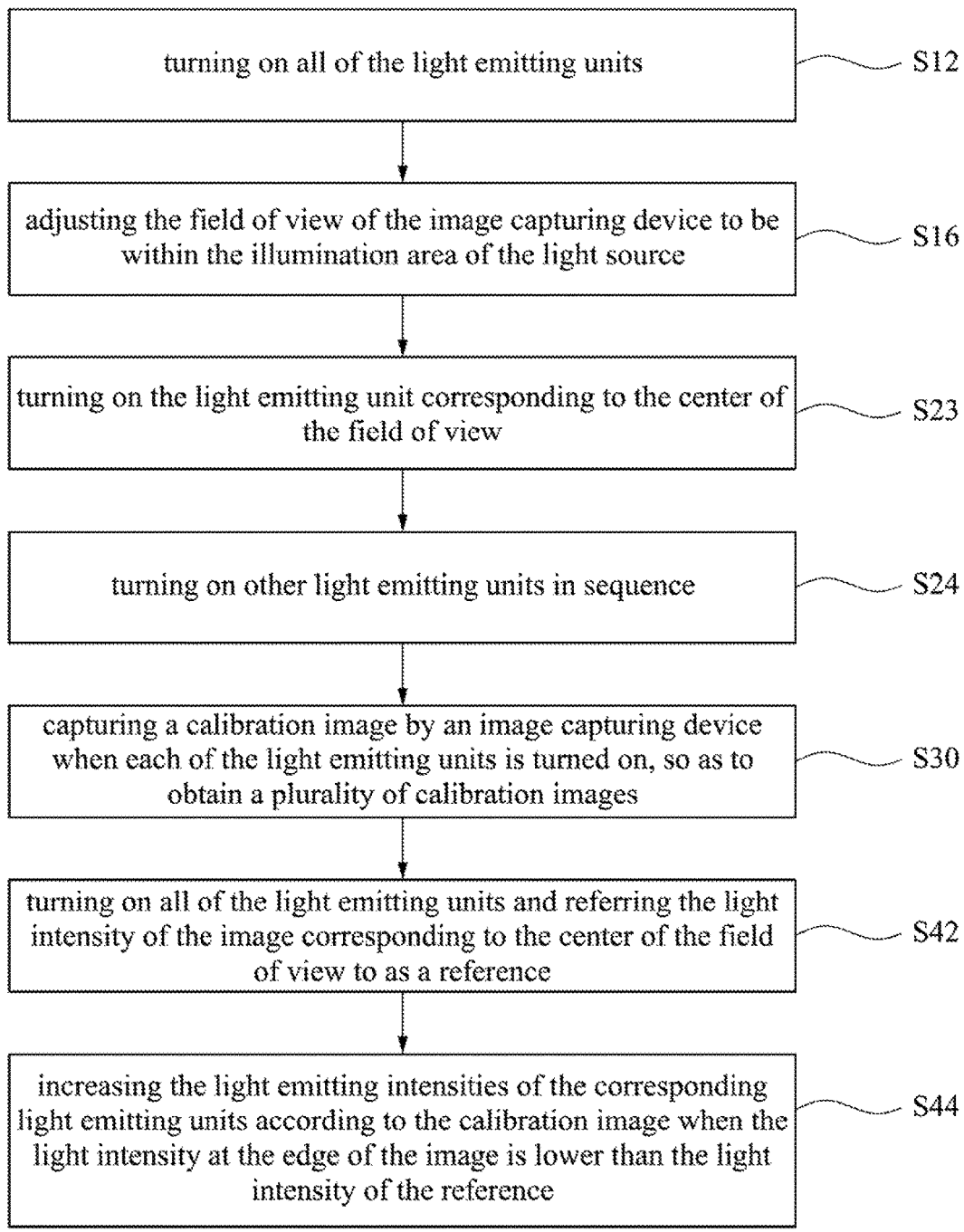
FIG. 5 is a flowchart of method for calibrating the light source of the inspection system of FIG. 1 according to yet another embodiment of the present disclosure.

FIG. 5 is a flowchart of a method for calibrating the light source 110 of the inspection system of FIG. 1 according to yet another embodiment of the present disclosure. Reference is made to FIGS. 1 and 5. In this embodiment, details of the step S10 in FIG. 2 are described from step S12. All of the light emitting units 112 are turned on, and thus a location of the illumination area 115 can be defined on the measuring stage 140. Next, as shown in step S16, the field of view 125 is adjusted to be within the illumination area 115, so as to determine the location of the field of view 125. That is, in this embodiment, the center C2 of the field of view 125 is not certainly overlapped, with the center C1 of the illumination area 115, such that the light source 110 and the image capturing device 120 can be disposed in various ways. For example, a sample under test unable to be disposed in the center C1 of the illumination area 115 can be applied to the inspection system. Step S16 can be achieved by moving a relative position of the light source 110 and the image capturing device 120, changing the illumination method of the light source 110, or changing the location of the field of view 125 of the image capturing device 120.

Thereafter, details of the step S20 in FIG. 2 are described from step S23. The light emitting unit 112 corresponding to the center C2 of the field of view 125 is turned on. The light emitting unit 112 corresponding to the center C2 affects the field of view 125 most. Next, as shown in step S24, the of her light emitting units are turned on in sequence. For example, since the light emitting units 112 closer to the center C2 affects the field of view more, the corresponding light emitting units 112 can be turned on from the center C2 to the two opposite sides in sequence, so as to respectively obtain the light intensities of the field of view 125 affected by each of the light emitting units 112, as shown in step S30.

However, the aforementioned steps are only examples. Basically, an embodiment falls within the claimed scope as long as the calibration images CI of the light emitting units 112 can be obtained.

Next, details of the step S40 are described from step S42. All of the light emitting units 112 are turned on, and the light intensity of the image corresponding to the center C2 of the field of view 125 is referred to as a reference. Then, as shown in step S44, when the light intensity of the edge of the image is lower than the light intensity of the reference, the light emitting intensities of the corresponding light emitting units 112 are increased according to the calibration images CI. As mentioned above, the farther away from the center C2, the light intensity of the obtained image becomes lower due to the vignetting effect of the image capturing device 120. Therefore, according to a difference between the light intensity distributions of the calibration images CI and the reference, the light emitting intensities of the corresponding light emitting units 112 can be increased.

In conclusion, the inspection system of the embodiments can respectively control the light emitting intensities of the light emitting units in accordance with the field of view of the image capturing device, such that the inspection image in the visual filed has the specific light intensity distribution. More specifically, the controller can respectively adjust the light emitting intensities of the light emitting units according to the effect of the light emitting units on the field of view after the location of the field of view is determined, such that the darkened image resulted from the vignetting effect of the image capturing device is compensated, and the inspection image in the field of view has the specific light intensity distribution. In addition, the controller can respectively control the light emitting units, even the location or the size of the field of view of the image capturing device is changed, the controller can still adjust the light emitting intensities of the light emitting units according to the location or the size of the field of view, such that the light source has the specific light intensity distribution on the field of view. That is, the inspection system of the embodiment can be applied to image capturing devices having different vignettings. Moreover, the light source and the image capturing device can be disposed in various ways by adjusting the light intensity distribution of the inspection image depending on requirements of the sample under test.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for an inspection system obtaining an adjusted light intensity image, the inspection system comprising a light source, an image capturing device, and a controller, the method comprising:
    adjusting a field of view of the image capturing device to be within an illumination area of the light source;
    turning on a plurality of light emitting units of the light source in sequence;
    capturing a calibration image of the field of view of the image capturing device when each of the light emitting units is turned on, so as to obtain a plurality of calibration images; and
    adjusting light emitting intensities of the light emitting units respectively by the controller according to light intensity distributions of the calibration images, so as to obtain an inspection image in the field of view having a specific light intensity distribution, wherein adjusting the light emitting intensities of the light emitting units respectively by the controller according to the light intensity distributions of the calibration images comprises:
        turning on all of the light emitting units and referring to a light intensity of an image corresponding to the center of the illumination area as a reference; and
        increasing the light emitting intensities of the light emitting units according to the calibration images when a light intensity at an edge of the image is lower than a light intensity of the reference.

2. The method of claim 1, wherein the inspection image has a uniform light intensity distribution.

3. The method of claim 1, wherein adjusting the field of view of the image capturing device to be within the illumination area of the light source comprises:
    turning on all of the light emitting units; and
    overlapping a center of the field of view and a center of the illumination area.

4. The method of claim 3, wherein turning on a plurality of the light emitting units of the light source in sequence comprises:
    turning on the light emitting unit corresponding to the center of the illumination area; and
    turning on the other light emitting units in sequence.

5. The method of claim 1, wherein adjusting the field of view of the image capturing device in the illumination area of the light source comprises:
    turning on all of the light emitting units; and
    adjusting the field of view of the image capturing device to be within the illumination area of the light source.

6. The method of claim 5, wherein turning on the light emitting units of the light source in sequence comprises:
    turning on the light emitting unit corresponding to a center of the field of view; and
    turning on the other light emitting units in sequence.

7. An inspection system for obtaining an adjusted light intensity image, comprising:
    a light source comprising a plurality of light emitting units, wherein the light source has an illumination area;
    an image capturing device having a field of view smaller than the illumination area; and
    a controller electrically connected to the image capturing device and the light source, wherein the image capturing device is controlled to capture a calibration image of the field of view of the image capturing device when each of the light emitting units is turned on, so as to obtain a plurality of calibration images, and light emitting intensities of the light emitting units are adjusted respectively according to light intensity distributions of the calibration images, so as to obtain an inspection image in the field of view having a specific light distribution, wherein the controller turns on all of the light emitting units, refers to a light intensity of an image corresponding to a center of the field of view as a reference, and increases the light emitting intensities of the corresponding light emitting units according to the calibration images when a light intensity at an edge of the image is lower than a light intensity of the reference.

8. The inspection system of claim 7, wherein the inspection image has a uniform light intensity distribution.

9. The inspection system of claim 7, wherein the controller turns on all of the light emitting units and controls the image capturing device to capture the inspection image.

* * * * *